US011120906B2

(12) United States Patent
Gandy et al.

(10) Patent No.: US 11,120,906 B2
(45) Date of Patent: Sep. 14, 2021

(54) SYSTEM FOR IMPROVING PATIENT MEDICAL TREATMENT PLAN COMPLIANCE

(71) Applicant: Play-it Health, Inc., Kansas City, KS (US)

(72) Inventors: Kimberly L. Gandy, Kansas City, KS (US); George Campbell, Greenville, SC (US)

(73) Assignee: Play-it Health, Inc., Overland Park, KS (US)

( * ) Notice: Subject to any disclaimer, the term of this patent is extended or adjusted under 35 U.S.C. 154(b) by 381 days.

(21) Appl. No.: 15/789,484

(22) Filed: Oct. 20, 2017

(65) Prior Publication Data

US 2018/0113985 A1 Apr. 26, 2018

Related U.S. Application Data

(60) Provisional application No. 62/410,663, filed on Oct. 20, 2016.

(51) Int. Cl.
| | |
|---|---|
| *G16H 40/63* | (2018.01) |
| *G09B 7/00* | (2006.01) |
| *G16H 50/30* | (2018.01) |
| *G09B 5/06* | (2006.01) |
| *G06Q 10/10* | (2012.01) |
| *G16H 20/10* | (2018.01) |
| *G16H 20/60* | (2018.01) |

(Continued)

(52) U.S. Cl.
CPC .............. *G16H 40/63* (2018.01); *G09B 7/00* (2013.01); *G09B 19/00* (2013.01); *G16H 20/00* (2018.01); *G16H 20/10* (2018.01);
*G16H 20/60* (2018.01); *G16H 50/30* (2018.01); *G06Q 10/1095* (2013.01); *G09B 5/06* (2013.01)

(58) Field of Classification Search
CPC .......... G16H 40/63; G16H 50/30; G09B 7/00; G09B 19/00; G09B 5/06; G06Q 10/1095; G06Q 50/22; G06Q 50/24; G06F 19/30; G06F 19/32; G06F 19/34
USPC ........................................................ 705/2, 3
See application file for complete search history.

(56) References Cited

U.S. PATENT DOCUMENTS

| | | | |
|---|---|---|---|
| 2010/0235196 A1* | 9/2010 | Bartholomew, III | ....................... G06F 19/3456 705/3 |
| 2012/0129139 A1* | 5/2012 | Partovi | ............... G06F 19/3418 434/262 |

(Continued)

FOREIGN PATENT DOCUMENTS

WO WO-2018034913 A1 * 2/2018 ............. G16H 50/30

OTHER PUBLICATIONS

Deborah J. Toobert et al., "The Summary of Diabetes Self-Care Activities Measure", Jul. 2000, Diabetes Care, vol. 23, No. 7. (Year: 2000).*

*Primary Examiner* — Elaine Gort
*Assistant Examiner* — Amanda R. Covington
(74) *Attorney, Agent, or Firm* — Erise IP, P.A.

(57) ABSTRACT

Systems and methods for generating a graphical interface and tracking patient adherence to a medical treatment plan are presented. The graphical interface may present to a patient the medical treatment plan. The patient may receive scores and points based on adherence to the medical treat- (Continued)

ment plan. The medical treatment plan may be updated based on the patient's scores, adherence to the medical treatment plan, and progress.

20 Claims, 8 Drawing Sheets

(51) Int. Cl.
*G16H 20/00* (2018.01)
*G09B 19/00* (2006.01)

(56) References Cited

U.S. PATENT DOCUMENTS

| | | | |
|---|---|---|---|
| 2015/0106369 A1* | 4/2015 | Nolan | G06F 16/9535 |
| | | | 707/732 |
| 2015/0242585 A1* | 8/2015 | Spiegel | G06F 19/3418 |
| | | | 705/2 |
| 2016/0098533 A1* | 4/2016 | Jackson | G06F 19/3456 |
| | | | 705/3 |
| 2016/0358116 A1* | 12/2016 | Cline | G06Q 10/06398 |
| 2017/0024546 A1* | 1/2017 | Schmidt | G06F 19/324 |
| 2017/0169185 A1* | 6/2017 | Weng | G06Q 10/1093 |
| 2017/0235909 A1* | 8/2017 | Lozano | G06F 19/3418 |
| | | | 705/3 |
| 2017/0286621 A1* | 10/2017 | Cox | G16H 50/30 |
| 2018/0176331 A1* | 6/2018 | Jain | H04L 67/327 |

\* cited by examiner

| Clinical Category | Default Watch | Default Danger | Default Nephrology Watch | Default Nephrology Danger | Default Transplant Watch | Default Transplant Danger |
|---|---|---|---|---|---|---|
| Pearls | 80 | 70 | 80 | 70 | 80 | 70 |
| Appointments | 80 | 70 | 80 | 70 | 90 | 80 |
| Labs | 80 | 70 | 80 | 70 | 90 | 80 |
| Medications | 80 | 70 | 80 | 70 | 90 | 85 |
| Total | 70 | 65 | 70 | 65 | 85 | 78 |

| | Schedule I | Pts | Schedule II | Pts | Schedule III | Pts |
|---|---|---|---|---|---|---|
| 702 | | | | | | |
| 704 | Evenly Weighted | | Education Weighted | | Weighted for Medications | |
| 706 | Pearls | | Pearls | | Pearls | |
| | Right on first try | 5 | Right on first try | 10 | Right on first try | 10 |
| | Right on second try | 3 | Right on second try | 5 | Right on second try | 5 |
| | Right after 2nd | 1 | Right after 2nd | 1 | Right after 2nd | 1 |
| 708 | Appointments | | Appointments | | Appointments | |
| | Clinic | 10 | Clinic | 10 | Clinic | 10 |
| | Lab | 10 | | | | |
| 710 | Labs | | Labs | | Labs | |
| | Spirometry | 10 | Lab | 10 | Lab | 10 |
| | Weight | 10 | | | | |
| | BP | 10 | | | | |
| | Glucometer | 10 | | | | |
| 712 | Medications | | Medications | | Medications | |
| | Taken within 30 min | 5 | Taken within 30 min | 5 | Taken within 30 min | 10 |
| | Taken on day | 3 | Taken on day | 3 | Taken on day | 5 |
| | Not taken, but reason given | 1 | Not taken, but reason given | 1 | Not taken, but reason given | 3 |
| 714 | Bonus, all meds in a day w/in window | 10 | Bonus, all meds in a day w/in window | 10 | Bonus, all meds in a day w/in window | 20 |

FIG. 8

SYSTEM FOR IMPROVING PATIENT MEDICAL TREATMENT PLAN COMPLIANCE

RELATED APPLICATIONS

This non-provisional patent application claims priority benefit, with regard to all common subject matter, of earlier-filed U.S. Provisional Patent Application No. 62/410,663, filed on Oct. 20, 2016, and entitled "SYSTEM FOR IMPROVING PATIENT MEDICAL PLAN TREATMENT COMPLIANCE." The identified earlier-filed provisional patent application is hereby incorporated by reference in its entirety into the present application.

BACKGROUND

1. Field

Embodiments of the invention relate to a system for improving the compliance with medical treatment plans by patients and facilitating real-time, actionable, indices in a concise format to medical providers for preventative and proactive care management.

2. Related Art

A significant portion of the United States population is aging and requires increased health care as a natural result. Additionally, there are patients that are subject to major medical procedures such as major surgeries, transplants and the like. Therefore, the reason for increased health care can be due not just to age, but also to catastrophic events such as injuries from accidents, birth, genetic defects, and so on. Such treatment can involve heart transplants, kidney transplants, bone marrow transplants, lung transplants and the like. Each of these is a significant medical undertaking and requires significant time and energy in the recovery process to prevent complication and adverse consequences. Many complications and adverse consequences can be avoided.

The problem of non-adherence to medical treatment plans, including medication regimens, is a problem to which much attention should be given. When investigating the reasons for non-adherence, it has been discovered that several factors are in play; lack of education, inadequate reminder systems, and infrequent interaction with health care providers, financial resources, and transportation inadequacies. The typical patient does not meet with his or her health care providers on a daily basis, but only receives feedback periodically about the effect of non-adherence and does not receive proactive information that would support adherence. Further, the education of the patient by the health care provider typically does not include feedback or reinforcement. Feedback and reinforcement are two of the most pivotal concepts in learning. Feedback involves providing learners with information about their responses, whereas reinforcement affects the tendency to make a specific response again. Feedback can be positive, negative or neutral; reinforcement is either positive (increases the response) or negative (decreases the response). Feedback is almost always considered external while reinforcement can be external or intrinsic (i.e., generated by the individual). The nature of the feedback or reinforcement provided was the basis for many early studies including those conducted in the 1960s. It was discovered that the use of "prompting" (i.e., providing hints) was recommended in order to "shape" (i.e., selectively reinforce) the correct responses. Other principles concerned the choice of an appropriate "step size" (i.e., how much information to present at once) and how often feedback or reinforcement should be provided.

SUMMARY

Embodiments of the invention solve the above-mentioned problems by providing a system for promoting adherence to medical treatment plans and compliance with such plans by providing a graphical user interface that makes handling all aspects of the medical treatment plan simple and clear.

A first embodiment of the invention is directed to a computer-storage media storing computer-executable instructions that, when executed by a processor, perform a method of tracking patent medical treatment plan compliance. The method may comprise storing a patient profile having a compliance score, presenting a medical treatment plan to the patient via a graphical user interface. Educational material as well as educational questions may be provided to the patient and the patients answer may be scored. The patient's attendance to medical appoints, lab results, use of peripheral devices, and medication taking may also be scored. The scores may then be added to the compliance score and the medical treatment plan may be updated based on the scores.

A second embodiment of the invention is directed to a method of tracking patient medical treatment plan compliance. A medical treatment plan may be generated and presented to a patient via a graphical user interface. An indicator of the patient's compliance with the medical treatment plan may be collected and a reward may be allotted to the patient for compliance. The medical treatment plan may be updated based on the indicator.

A third embodiment of the invention is directed to a method of tracking patient medical treatment plan compliance. A medical treatment plan may be generated and presented to a patient via a graphical user interface. An indicator of the patient's compliance with the medical treatment plan may be collected. The medical treatment plan may be updated based on the indicator. The indicator may be selected from a set comprising correctly answered questions by the patient, appointments attended by the patient, patent medical history, patient laboratory history, patient nutrition history, and patient data gathered by a peripheral device.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Figure 1:
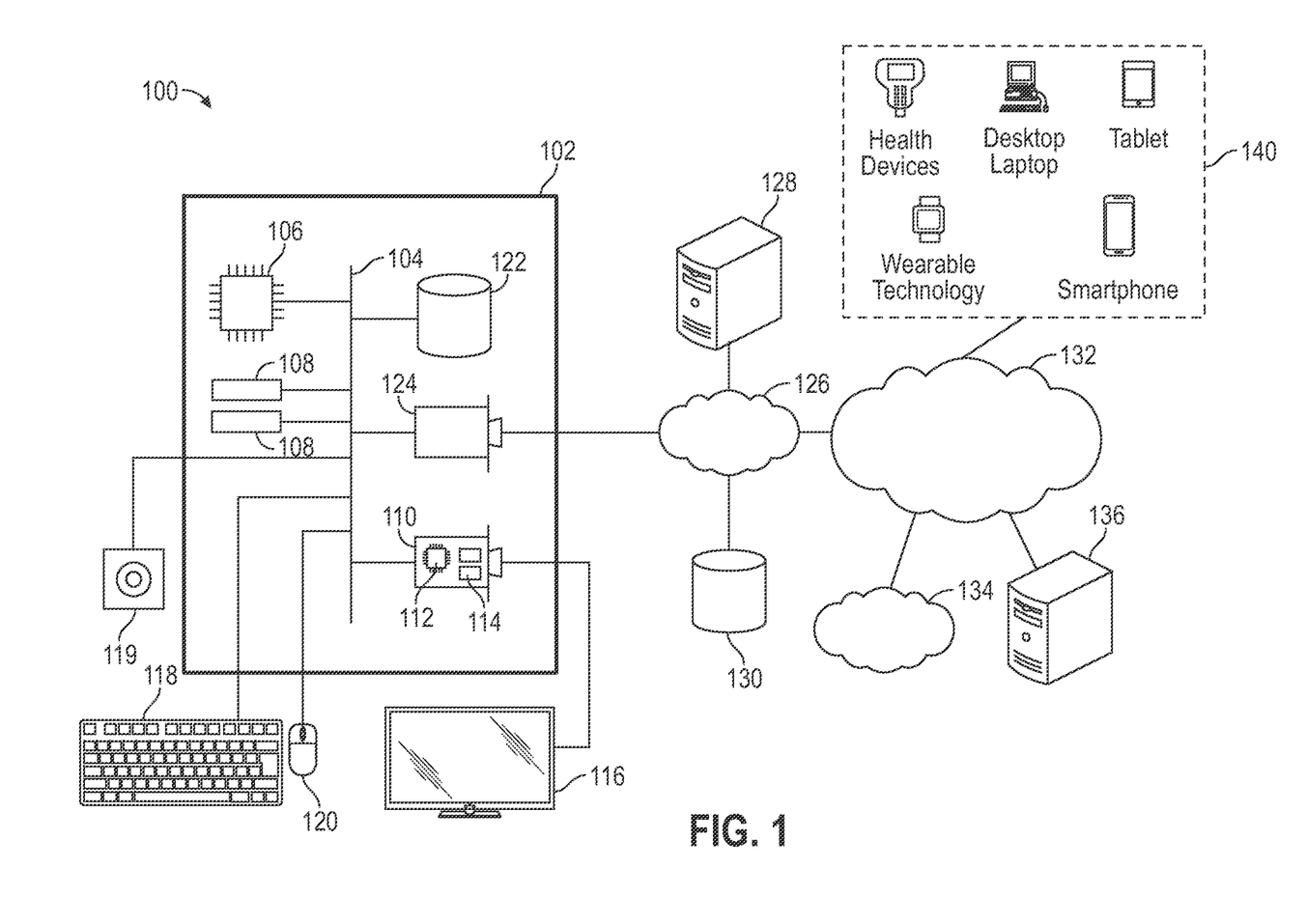
FIG. 1 depicts hardware used with embodiments of the invention.

Turning first to FIG. 1, an exemplary hardware platform 100 for certain embodiments of the invention is depicted. Computer 102 can be a desktop computer, a laptop computer, a server computer, a mobile device such as a smartphone or tablet, or any other form factor of general- or special-purpose computing device that may have a touch, sound, or visual interface. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also, attached to system bus 104 are one or more random-access memory (RAM) modules 108. Also, attached to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also, connected to system bus 104 is local storage 122, which may be any form of computer-readable media, and may be internally installed in computer 102 or externally and removeably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

In embodiments, data from wearables may be periodically collected from a web-based cloud, such as server 130. Further yet, data may be transmitted to the system from larger appliances such as infusion pumps, ventilators, treadmills, electronic scales, in home devices or from healthcare facilities. Embodiments of the invention may be communicatively coupled with and draw data from facility-wide structures, such as nurse call systems, interactive patient beds, and real-time location systems. The communications can be a direct wired communication, wireless connection, local area network, wide area network or any combination of these. The above data sources are intended only to be exemplary and are in no way meant to limit the invention. Data acquired by any means from any source may be used in the embodiments of the invention.

A user, in an exemplary embodiment depicted herein, the user is a patient, may create or log onto a patient profile via a graphical user interface. The patient profile may access personal information including medical information included in embodiments of the invention. A medical practitioner may have access to a portion, all, or more information than the patient on the patient profile. The patient profile may contain confidential information, but other patients as allowed by the patient, may have access to all or a portion of the information. This may be helpful in competitions or gaming scenarios. Relatives or guardians may be granted access as well. The patient profile may be linked and gather data from online datasets such as social media, geographical location maps, and available healthcare historical datasets. The data collected and stored on the patient profile may also be accessible for statistical analysis to build better algorithms and improve patient care. The patient and the medical practitioner may communicate via the GUI by any form of messaging, telephony, email, or the like.

The patient profile may store information indicative of the patient's adherence to a patient medical plan. The patient medical plan may be administered by the medical practitioner. The patient medical plan may be a standard model, a model built on statistics from historical data, customized to the patient, or may be any combination of these. The patient plan may have been formed by medical practitioners or from statistical or machine learning algorithms. The patient plan may consist of but is not limited to multiple components such as educational, appointment, laboratory work, linked peripheral device, medication, and nutrition. The plan may be dynamically changing with the patient's adherence to the plan and medical progress. The patient profile may store points associated with the level of adherence to the plan. The points may be used for such benefits as reduced insurance premiums, reduced copays, rebates, coupons, reduced price groceries, or any other product that may be in demand by the patient.

A compliance score may be used to indicate the overall compliance or adherence of the patient to the medical treatment plan. The compliance score may be made up of several individual indicators or components that may be used. In embodiments of the invention, indicators and components used include a pearl score (e.g. a first score), appointments (e.g. a second score), labs (e.g. a third score), and medications (e.g. a fourth score) which may be referred to collectively as an acronym "PALM". A PALM score, being an exemplary compliance score, may represent the compliance and adherence to a medical treatment plan by comparing the PALM indicators with the medical treatment plan events and can be used to assess, predict, or represent the risk of complications and therefore the cost of healthcare or future health care for the patient. The PALM score can also be used by entities such as insurance companies to determine a premium for a customer. For example, one with a higher PALM score would expect to have fewer complications or relapses from health care than one with a lower PALM score.

It should be noted that any individual indicator may be used independently from any other indicator. The indicators may also be used in any combination that best exemplifies a patient's compliance to the medical treatment plan.

The compliance score, exemplified by the PALM score, can be expressed in any of several forms. A first exemplary form is a numerical value. The numerical value could be expressed from −100 to +100, such that −100 is completely noncompliant and +100 is completely compliant (intermediate values being in the range of −99 to 0 and 0 to +99). In other embodiments, the numerical value could be expressed a likelihood from 0-10, such that 0 is completely noncompliant and 10 is completely compliant (intermediate values ranging from 0.1 to 9.9 or 1 to 9). In yet other embodiments, the numerical value is a summation of factors with no theoretical maximum or theoretical minimum. A second exemplary form is a letter grade, such as an "F" for completely noncompliant and an "A" for completely compliant (intermediate values being "B," "C," and "D"— possibly including plusses and minuses). A third exemplary form may be a color system in which red is completely noncompliant and green is completely compliant (intermediate values being on the color spectrum between red and green). A fourth exemplary form may be a simple pass/fail designation. The pass/fail designation definitely states whether the system believes the user to be compliant or not. In this and other forms, the system may presume that the user is compliant until proven uncompliant (or vice versa). A fifth exemplary form may be a graphical representation as discussed below.

The PALM score can be used to stratify patients in relation to risk of non-adherence which therefore can result in a determination of the risk of incurring increased health expenditures and the need for increased surveillance such as telemedicine, direct medication use, monitoring technology, and the like. Insurance companies may also use the PALM score to provide rebates to patients that adhere to the plan. Successful adherence may warrant a decrease in medical costs if a patient supersedes the predicted PALM score. An insurance provider may use the PALM score for any data outside the scope presented herein. Moreover, the continued comparison of the PALM score to claims and other outcomes data may validate the PALM score as an indicator of total health.

It should be noted that the overall PALM score may be used for assessment or as an indication of a patient's adherence and compliance to the medical plan, but each individual indicator may be used independently as well. As in the above example, the insurance provider may use the PALM score to make determinations on premiums, rebates, or other charges. Using the overall PALM score is exemplary and any of the individual indicators representing PALM, e.g. the Pearl, Appointment, Labs, Medications or any other individual indicators that may be added may also be used. The individual indicators may be used collectively, individually, or in any combination useful to any entity such as an insurance provider, healthcare provider, or patient that may be most useful, or necessary. The PALM score may be dynamically changing as it is updated with new patient information hourly, daily, weekly, or however often to best judge a patient's adherence.

A predictive tool may be used to determine the patients most at risk for nonadherence. This may be called predictive PALM or (PALM$^P$) and may use such indicators as a patient's demographics, appointments, labs, and medications. Retrospective data may be used in concert with an algorithm to predict the patients most at risk. To have a large amount of data across many different demographics, data from multiple health care providers from many different locations may be used. The prediction may be determined by health care practitioners reviewing the statistics and determining where a patient falls relative to the data. The predictions may also be determined by computer based algorithms using any statistical filtering or machine learning algorithms. As an example, HgA1c is a value that indicates how well one's blood sugar has been controlled. It is commonly used in diabetes. It also has been shown to have correlations in heart failure. This indicator may have predictive power over multiple chronic conditions in patients with diabetes. It may also be an indicator for patients without diabetes.

A medical treatment plan may be issued to a patient based on the predictive PALM and customized using the patient's medical history and demographics. The medical treatment plan may be updated dynamically by the patient's adherence to the plan and the progress of the patient.

Figure 2:
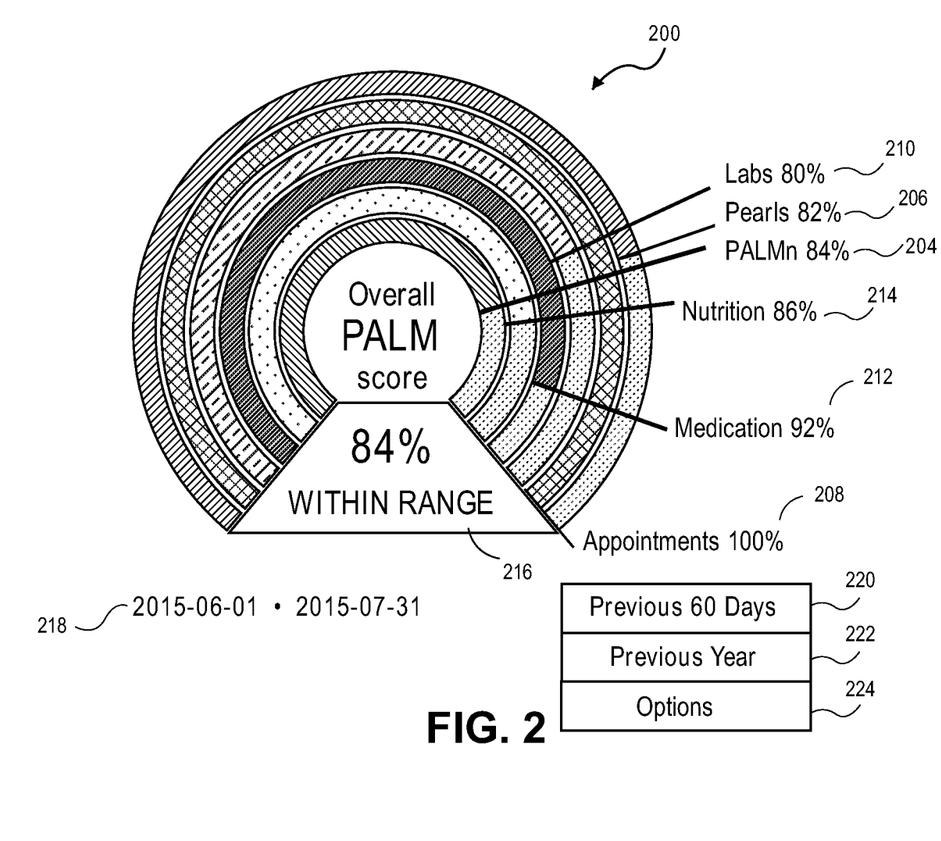
FIG. 2 depicts an exemplary graphical user interface displaying an embodiment of the invention.

FIG. 2 depicts an exemplary graphical user interface (GUI) of an embodiment of a GUI depicting PALM display 200. The PALM display 200 may present an overall PALM score 204 (shown as 84%) that is a combination of several other components or PALM indicators. The PALM display 200 may be graphically represented in circular "speedometer" form, in bar graph form, as a pie chart, a line graph, thermometer, or any other method that may present the data and be easily understood. The exemplary GUI display depicted in FIG. 2 is circular.

The PALM score 204, as depicted in FIG. 2, includes components or PALM score indicators such as Pearl score 206, Appointment score 208, Lab score 210 and Medication score 212 (collectively "PALM"). Nutrition score 214 is an additional available component indicative of a patient's diet, that would be indicated with a "n" in superscript to the term "PALM." It should also be noted that the acronyms are exemplary. For example, in embodiments, the "n" may stand for nutrition, but this may also be replaced with "d" for diet while providing the same or similar function or evaluation.

The Pearls may be content that is generated from a central service or other remote server and be transmitted to a smart phone or other personal computing device that may have a touch, sound, or visual interface and include medical educational content or internet accessibility. Under a feedback and reinforcement method of education, the individual patient may be asked a question and a determination can be made whether the answer from the individual/patient is correct. This assessment is independent of the number of times the individual attempts to correctly answer the questions. For example, there may be a point degradation schedule where one gets 4 points in the event they get the question right on the first try, and the points decrease upon further attempts. Therefore, the points accumulated by the individual can be used to determine the Pearl score 206 on a periodic basis. For example, a rolling week, aggregate for a month, or other timeline that may be chosen by a medical practitioner or patient that may be customized for a particular patient. The time-period may also be the same for all patients to get a normalized model to compare patients.

The Appointment score 208 is derived as to whether the individual attended a scheduled appointment with a health care provider or not. An appointment is scheduled through the health care provider and the central server can access or receive data from an information system of the healthcare provider and populate a database linking the individual with a scheduled appointment. The appointment information may be used to operatively coordinate with the reminder system of the individual to remind the individual of the appointment. For example, the central server can transmit appointment information by any messaging, email, social media and the like, and create an appointment and reminder that can be displayed on the personal computer device of the individual. The individual may be provided points for keeping appointments and may be provided no score for missing an appointment. Appointments may be rescheduled without losing points or may be given an amount of points between the full predetermined amount and zero. When the appointment is kept, the health care provider updates its database and such information can be transmitted to the central server indicating whether the individual kept or missed the appointment. The central server can determine the score from this information and the score may be displayed as the appointment score 208.

The Lab score 210 may be based on the information from medical lab results and various measurement devices. Such medical devices may include glucometers, blood pressure cuffs, spirometers and other peripheral devices. Information from these devices may be transmitted to, received from, or otherwise gathered and stored on the personal computer device, smart phone, or central server. By using an interface with the peripheral devices, it is possible to retrieve, store, and use information from many devices. It should be noted that when a lab appointment is scheduled to take samples (blood, urine and the like), the lab appointment can be scheduled in the appointment functionality of the invention.

The individual indicator "L" may also represent linked peripheral devices. A score may be provided for a patient based on devices that measure and store information indicative of a patient's activities or health. The peripheral devices may be health monitoring equipment such as a heart monitor, glucometer, insulin pump, thermometer, or any health monitoring equipment that may be in home or in a medical facility. The peripheral devices may also be exercise or wearable devices such as an elliptical, treadmill, pedometer, smart watch, smart phone, GPS, or other device that may track a patient's exercise or health progress.

The medication score 212 may be based on whether the individual is taking the prescribed medication. In an embodiment, the timing of taking the medication is a factor in the medication score 212. A point system may include, for example, 5 points for taking medication within the prescribed time window, 3 points for taking the medication at all and 1 point for indicating why the medication was not taken.

An optional nutrition score 214, indicated with a "n" in superscript at the end of the term PALM e.g. "PALM", is based on the actual food intake of the individual as compared to a specific regimen tailored to the specific diseases or conditions of the individual. The system may incorporate optical recognition software to recognize types of food and compare those results with user input. This food engine may factor the color, proportion, and texture in relation to surrounding objects contained in the image, geo-location information, time and date of the image capture, time between image creation and transmission, and other food images previously submitted by the user as compared with the images submitted by all users.

An optional symptom score may also be used similarly to the nutrition score. The patient's symptoms may be tracked and graded. The symptoms may come from a list of symptoms and be tracked as present or not present. The symptoms may be input into the system by the patient or the medical practitioner based on how the patient feels or a medical examination. The grades given to the symptom score may be binary or any other scoring technique described above. Some symptoms will be tracked with severity such as shortness of breath or pain while walking (claudication). The symptom tracker may be implemented in the predictive features for determining patient conditions as well as predicting patient adherence and compliance. The symptoms score may be updated regularly dynamically as the symptoms change. A score may be associated with the symptoms as described with the other indicators above. The symptom score may be incorporated into the PALM indicated as $PALM^S$ or PALMS. The overall PALM score may also be calculated using the symptom score along with any other indicators including nutrition.

Continuing with the embodiment depicted in FIG. 2, the overall palm score 204 is also depicted in block 216. The overall PALM score 204 is 84% and labeled "within range" in block 216. "Within range" indicates that an alert is not required. The PALM score 204 may fall below a certain predetermined threshold indicating a different designation. For example, the PALM score 204 may fall below 80% indicating a "watch" or "warning" designation. A "watch" designation may indicate that the PALM score 204 has fallen below a first threshold and attention is need. The PALM score 204 may fall below 70% indicating a "danger" designation triggering an immediate attention alert be sent to both the patient and a medical practitioner. The threshold values may be any number as decided by the medical practitioner, the patient, or statistics of historical data. The designations may be any word or phrase that best represents the state of adherence or condition. A level of may be present that activates an automatic emergency alert at the closest, or a saved, medical facility.

A date range 218 may give the current date or the date range 218 that represents the time frame the PALM score 204 is tabulated. The time frame may be changed to any range by touching the dates and typing in or selecting from a calendar. There may also be quick selection options presented as in blocks 220 and 222. These quick selection numbers may be any predetermined range. The date range 218 may be updated automatically based on the set range selected in blocks 220 and 222.

The options block 224 may provide access to settings such as other GUI formats, display, audio, video, communications, alerts, charts, contacts, healthcare billing, medical records, designation levels, the patient medical plan charts and designations. The patient may be able to change any information in the options. A medical practitioner with access to the patient profile may also be able to access and change the information on the options menu. The feature may also contain a quick call feature to contact the medical practitioner with an urgent telemedicine session. The call may be via phone or video and may access the phone features and the contracts if the device is a mobile phone.

Block 216 may also be a particular color corresponding to a range in which the PALM score 204 falls. For example, a "within range" designation may be a green color and a "danger" designation may be a red color. In embodiments, colors may be yellow, gold, brown, purple, pink, or any color that may be used to indicate a designation. The displayed score in block 216 may also be any of the individual components or indicator scores. The color of the block 216 and an alert may be indicative of the indicator in the block 216. For example, the patient may wish to look specifically at the labs score 210. The patient may touch the block 216 displaying options to choose from a list of components of the PALM score 204. The patient may choose the lab score 210 displaying the lab score 210 in the block 216 and changing the color of block 216 designated by the level of the lab score 210. In the event the lab score is in a danger zone then "danger" may be displayed along with an audible alert and a message sent via email, messenger, or the like.

The circular blocks depicting individual indicator scores pearls 206, appointments 208, labs 210, medication 212, and nutrition 214 may also be displayed in colors indicating warning, watch, normal, or danger levels. These colors may indicate that the individual numbers may have fallen below a particular threshold or level. For example, as depicted in FIG. 2, the Labs value is 80%. If the level for within range for the Labs has been set to 85% then the Labs value for the patient is at a lower level. This may be designated a "watch" level and the circular block indicating the lab score 210 may be colored yellow. Visual and auditory alerts may be produced when a change in level has occurred such as blinks, flashes, alarms, or a voice describing the condition.

The scoring system for all or any combination of PALM indicators may be the same or different based on the particular indicator. The scoring may be a binary system where points are allotted for completion and no points are allotted for incompletion, or vice versa. The points may also be awarded in a manner that generates a portion of the points for completing a portion of the task, as indicated above.

In embodiments, the scoring for individual indicators of the PALM assessment may be the following: Pearls and medications can be tabulated daily, weekly or any other date range. Appointments can be tabulated daily, weekly, monthly or any other date range. The tabulation can go for any predetermined time duration and can be dynamic, so that the individual can see changes in parameters to provide timely feedback and positive reinforcement.

The medical treatment plan comprising the PALM components may also be updated at any time with new information provided by historical data, new studies, or statistics. A patient's medical treatment plan may also be compared to medical treatment plans of other patients based on similar statistics and demographics.

Figure 3:
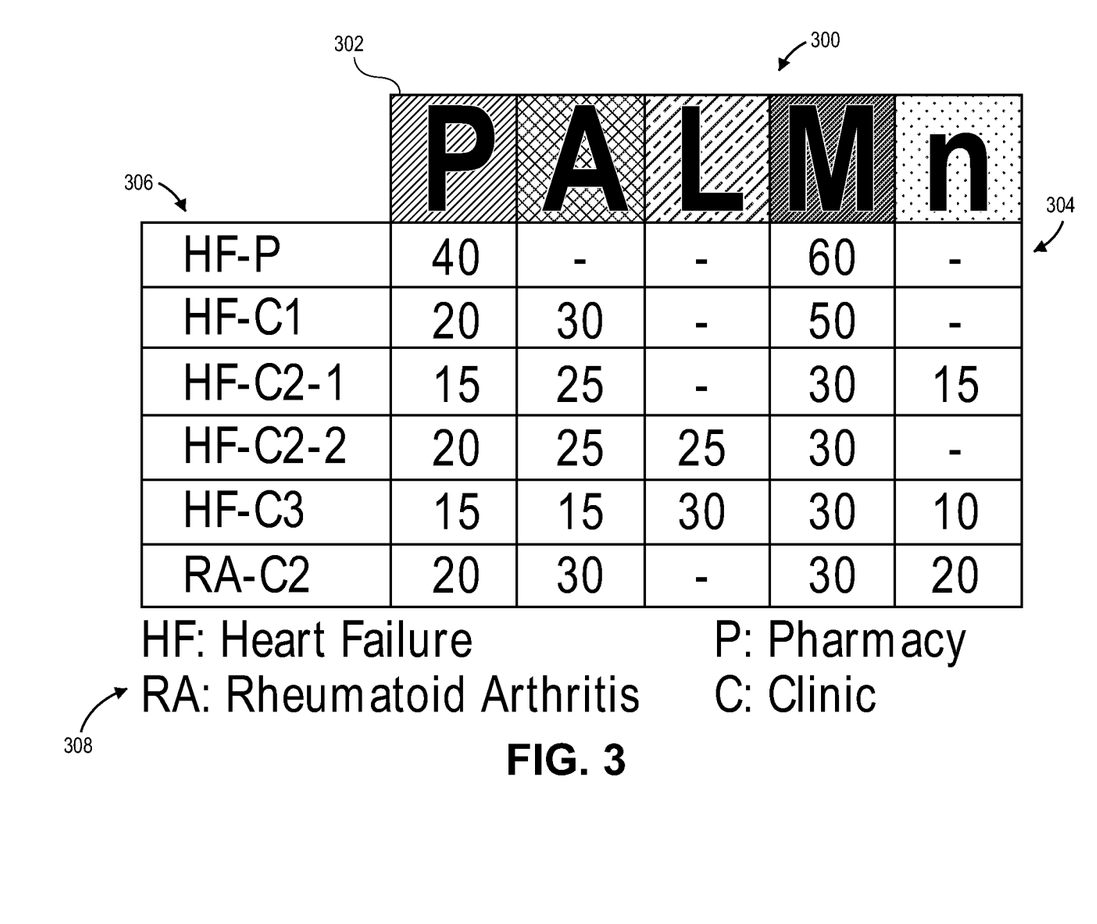
FIG. 3 depicts an exemplary weighting chart.

In embodiments, the calculation of the overall PALM score may be the sum of the components of the score, but with different weighting factors. FIG. 3 depicts an exemplary weighting chart of an embodiment of the invention. The weight of each of the components of the PALM may vary by a disease or chronic condition. This may be due to differing elements having different importance in the care of certain conditions. In some cases, it may not be important to monitor labs, where in others, labs are a critical component. For example, while all four elements may add up to 100% of the total PALM score, transplants may have the Pearls amount to 20% of the overall score, appointments 20%, labs 20%, and medications 40%. Each component or element has a percent related to total events due for that entity. For one example, if 25 meds are due in a week, and the patient took 24, then the patient has 96% of the total points, as a percentage, that can be achieved with the meds, or 38.4% of the total 40 points achievable.

The overall score may also be derived for individual institutions. For an exemplary institution, pearls can be 30%, appointments can be 30%, labs may not necessarily be applicable and medications can be 40%. Further, the only appointment score that may be included in the overall score may be the institutional appointment. As depicted in the exemplary weighting chart 300 in FIG. 3, PALM" heading 302 displays the columns that represent the different indicators and the associated weights 304. The column 306 indicates the condition and the location for treatment. The key for column 306 is located below at 308. The weights may be different for different locations even though the condition for the first five locations is heart failure. The lab only applies weights to Pearls and Medication since the other factors are not relevant in labs. The clinics weigh different combinations of all factors. As shown in FIG. 3, it is clear that rheumatoid arthritis (RA-C2) and heart failure (HF-C2-1) are weighted differently.

The conditions may also be weighted differently regardless of the locations. The weights may be based on the conditions and elements available for weighting. For example, appointments may have a weight of 20% in the PALM for transplant, but may only have a weight of 10% in rheumatology. Nutrition may have a weight of 10% for heart failure and 20% for rheumatology. Any differential weights may be applied to applicable indicators for any condition.

Moreover, the weighting of components may shift dynamically to apply greater weight to the components in which the patient is performing the worst or even less well in relational comparison to the other components, and this dynamic weight shifting may continue in real time, actively responding to the performance of the patient. For example, if the patient does well with medications one week and poorly with labs, but performs in the converse the following week, the PALM score for that patient may adjust the weight in real time as the shifting performance deficiencies are detected. Thus, the medical provider, patient and other stakeholders may also be able to view a "consistency factor" that attends each PALM score for an individual patient and for an overall health population.

Figure 4:
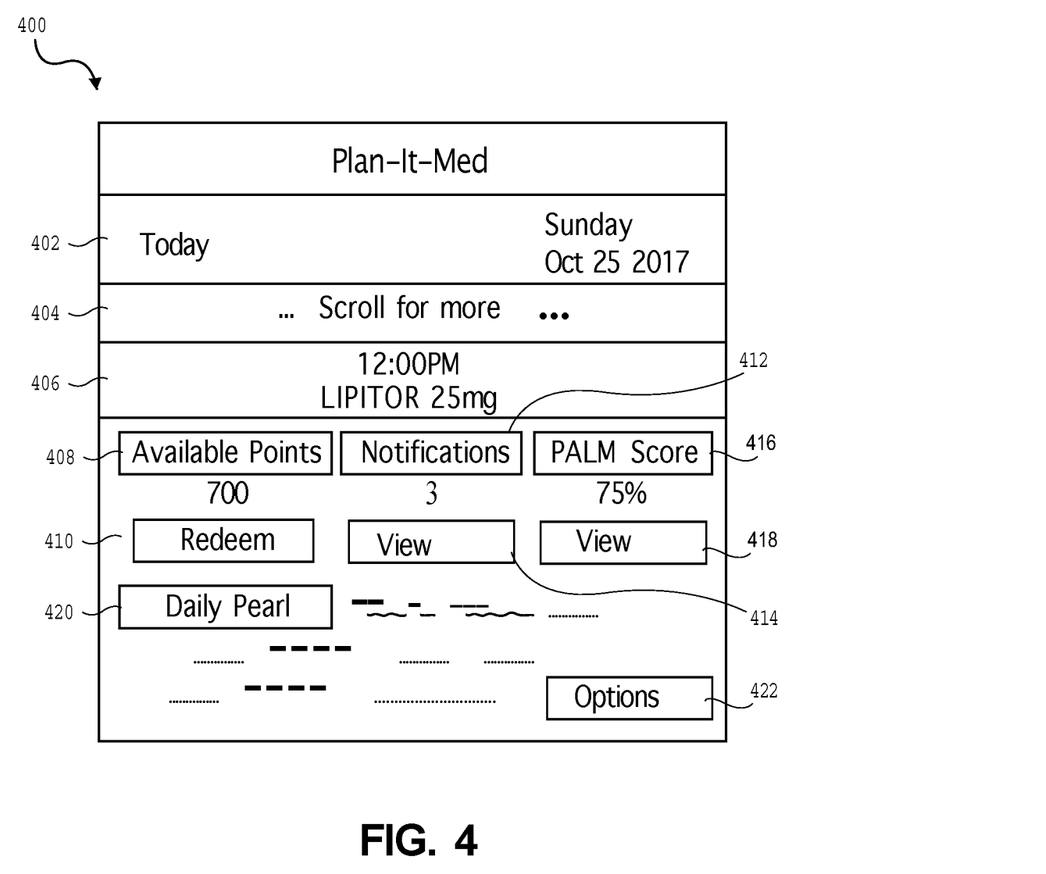
FIG. 4 depicts an exemplary graphical user interface displaying an embodiment of the invention.

FIG. 4 depicts an exemplary embodiment of a PALM graphical user interface 400. The embodiment depicted may provide easy visibility of date and time information in block 402. Using scroll 404 the patient may view scheduled times for a medication as depicted in block 406. Block 408 provides the available accrued PALM points that may be redeemed in block 410. PALM points may be redeemed for coupons, groceries, games, insurance premium or copay reductions, rebates, music, or any other incentive that may be useful to a patient. The points may also be available to other PALM patients and may be made into a competition. The patient with the highest score at the end of the competition may receive a reward. Notifications are presented in block 412. These may be automatic notifications such as reminders or alerts. The notifications may also be messages from the medical practitioner in the form of text, email, social media messenger, voice mail, or any other messaging method. The notifications may be viewed by touching the view button 414.

The PALM score is displayed below block 416. The independent indicators may be viewed by touching the view block 418. The PALM score may be highlighted in a color if one or more, or the overall PALM score, is below a threshold value. A daily Pearl is presented in block 420. The daily Pearl presents a question to the patient. The question may be regarding educational material that the patient has reviewed. Points may be allocated to the patient account based on how many times it takes the patient to correctly answer the question. The points may also be binary such as in the case of a yes or no, or a true or false answer. It should be noted that this is an exemplary embodiment and that the blocks may be in any order or arranged anywhere in the display. Likewise, not all blocks may be present or more may be added as needed. Blocks may not be rectangular but may be round triangular or any other shape. Blocks may be colored, tinted, or presented in any way that may be useful. An individual block may take up the entire screen for emphasis. For example, the daily pearl may be presented with a tactile, auditory, or visual indicator. The pearl may be presented in a specialized graphic or color. The pearl may be presented in any way that may help get the patient's attention.

For ease of use, the display in FIG. 4 may also present icons depicting the condition of the patient. For example, in the event that the overall PALM score is low an icon of a person not feeling well may be displayed. Alternatively, in the event the PALM score is high an image of a happy face or other such indicator may be displayed. The image may be automatically changed based on any individual indicator of the PALM score or may be changed by the patient or medical practitioner. This may be a quick reference to a patient wearing a smart watch or other portable device. This may also be a convenient reference for a medical practitioner that wants to quickly check in on a patient.

FIG. 4 represents one format for the user display 400 where the format for the display can be a default format or one customized to the individual with or without the input from the health care provider. In the event that the individual is not compliant or the scores are not high enough or are not to a certain level, the format can be changed using the options block 422 similar to the block 224 described above. With the modified display format, the individual may find the display more pleasing, functional, easier to read or otherwise be suited to provide assistance to the individual so that adherence to the medical treatment and action increases. Color or tint change or the display may change to a patient preference. Audible and visual alerts may also be adjusted. Through the options menu, the patient or medical practitioner may choose alternate display options.

Figure 5:
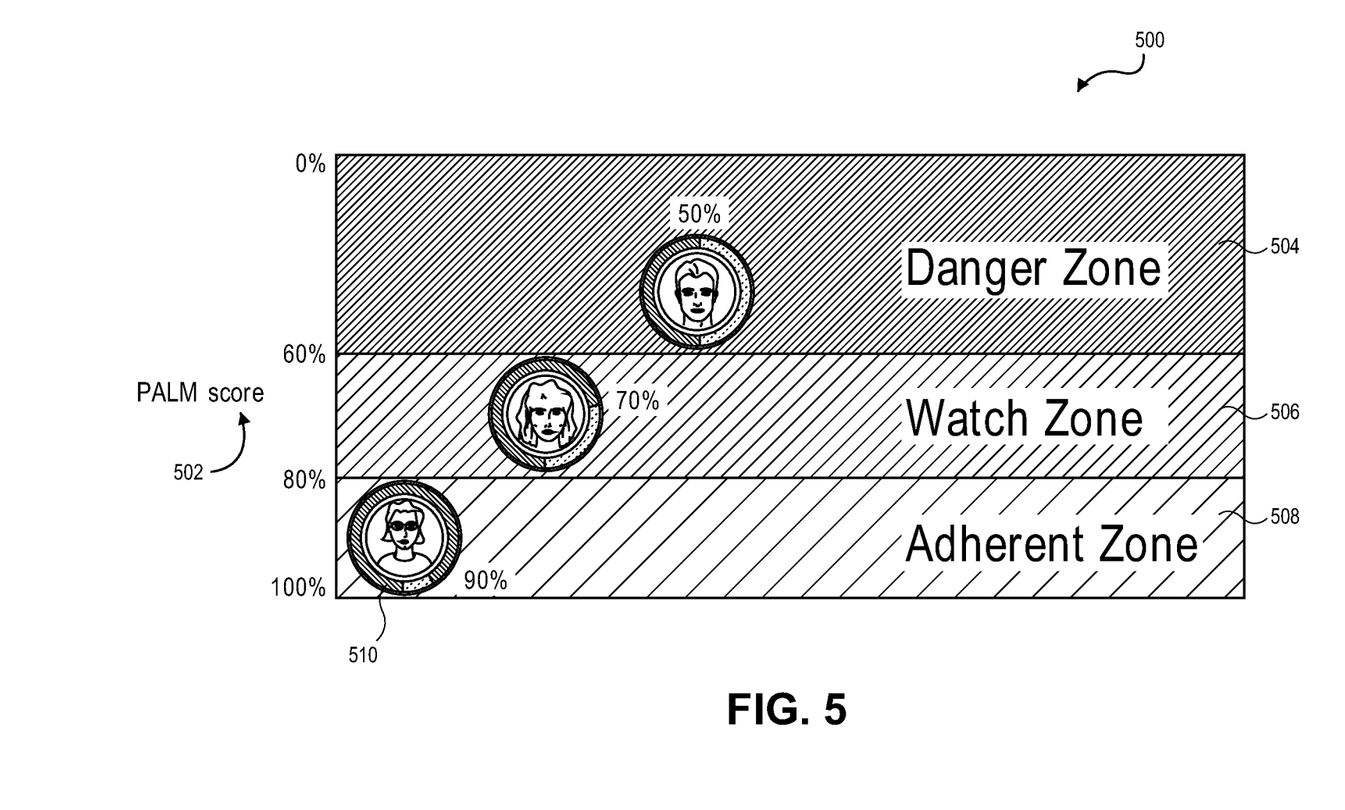
FIG. 5 depicts an exemplary graphical user interface displaying an embodiment of the invention.

In an exemplary embodiment depicted in FIG. 5, the medical practitioner's patients may be stratified on a PALM score display 500 displayed by the GUI. The medical practitioner may easily and quickly view which patients are in different zones, and which patients may need urgent attention. As depicted in FIG. 5 the PALM score 502 is broken up into different zones or thresholds. These zones are labeled Danger Zone 504, Watch Zone 506, and Adherent Zone 508. A patient picture 510, from the patient profiles, are displayed within each zone. By this method, the medical practitioner may easily and quickly see which patients are adhering to the plan and which may be in immediate need of attention. The medical practitioner may touch a patient's image to link to the patient profile or contact the patient.

The embodiment depicted in FIG. 5 may also be used by the patient. The patient pictures 510 may be replaced by the patient's individual indicators so the patient can easily see in the where the indicator falls on the heat map. This may help remind a patient that they missed an appointment or medication in the event that one of the PALM components changes levels on the chart. The levels may be different colors but also may blink, flash, and audible alerts may be transmitted at different levels.

Figure 6:
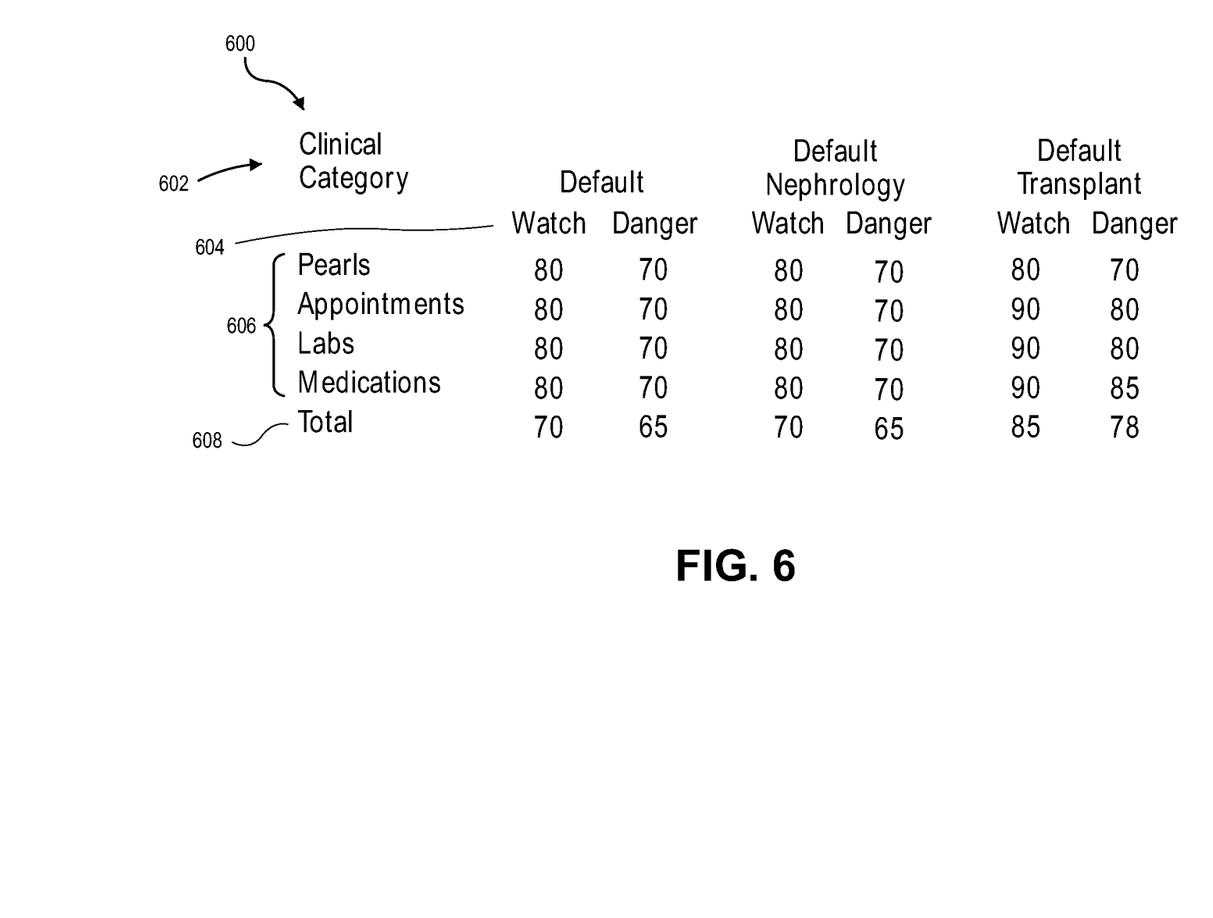
FIG. 6 depicts an exemplary levels chart.

Turning now to FIG. 6, an exemplary levels chart 600 is shown. The overall PALM score can be segmented into a range as depicted in level chart 600. For example, if the overall score is below a first level, an indicator (pink) may be displayed on the personal computer device or smart phone. If the overall score drops below a second level, such as a range designated as a danger zone an indication (red) may be displayed to the individual. Clinical categories 602 and "watch" and "danger levels" 604 may be illustrated in an embodiment as shown in FIG. 6. The first row is the header 602 comprising clinical categories and how the levels were distributed. "Default" indicates that the levels are set to default values. The levels may also be set by the medical practitioner or the patient. The levels may also be set by an algorithm based on historical data. The default levels depicted in FIG. 6 may be based on historical data. The PALM individual indicators 606 show different values for "watch" and "danger" as well as for the different clinical categories. The patient or medical practitioner may reference this chart to compare the patient's PALM scores to see if the patient is in the "watch" or "danger" levels for any of the individual indicators or the overall PALM score represented in FIG. 6 for comparison as Total 608. The levels may be customized as the disease or condition progresses as well as how the patient responds to a treatment. When the level chart 600 is updated any feature on the GUI representing the levels or threshold values may also be automatically updated. The levels table 600 may be accessible via the GUI options link represented in FIG. 2 block 224 and in FIG. 4 block 422.

Figure 7:
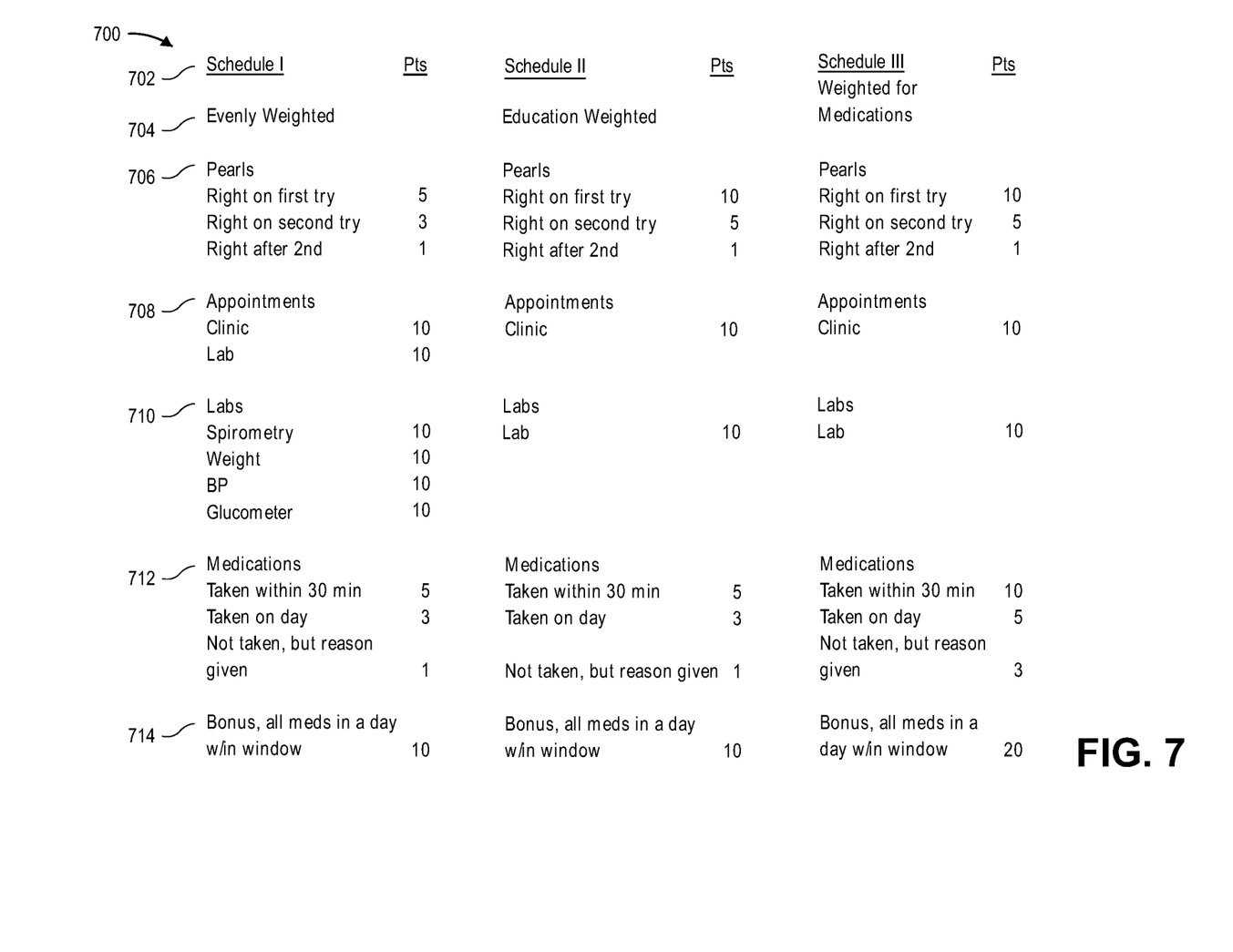
FIG. 7 depicts an exemplary scoring chart.

Turning now to an embodiment displayed on the GUI depicted in FIG. 7, the calculations for points provided on the point chart 700 may have the following functionality that can be accomplished by computer readable instructions that are stored on a computer-readable medium and when executed. The heading 702 displays three independent schedules and the location of the points in columns. Row 704 displays a designation for weighting for each of the schedules. Schedule I is evenly weighted giving all categories even importance. Schedule II is education weighted giving more importance to the pearls. Schedule III is medication weighted giving more importance to taking medications. The pearls scoring format is represented in row 706. The pearls are questions relating to education that were received by the patient. As depicted in Schedule I, the patient may receive 5 points for answering the question correctly on the first try, 3 points on the second try, and 1 point after the second try. The patient may be given a greater or fewer amount of points for answers depending on the weights. For example, Schedule II is education weighted. The patient may receive 10 points for a correct answer on the first try, 5 points for the second try, and 1 point for a correctly answered after the second try. 10 points may be allotted for meeting appointments 708 at both the clinic and lab. 10 points may also be allotted for lab work in the Lab row 710. The medications row 712 may value medication based on the time the medication was taken. For example, Schedules I and II allot 5 points if the medication is taken within 30 minutes of the prescribed time, 3 points if the medication is taken on the prescribed day, and 1 point if the medication is not taken but a reason is given for not taking the medication. Schedule III is medication weighted so the scoring may be different. For example, 10 points are given for taking the medication within 30 minutes of the prescribed time, 5 points are given for taking on the day of the prescribed time, and 1 point is given for not taking the medication but providing a valid reason. Bonuses 714 may also be given for taking all medication within a prescribed time period. Bonuses 714 may be in the form of more points or any of the possibilities for redeeming points as discussed above.

Figure 8:
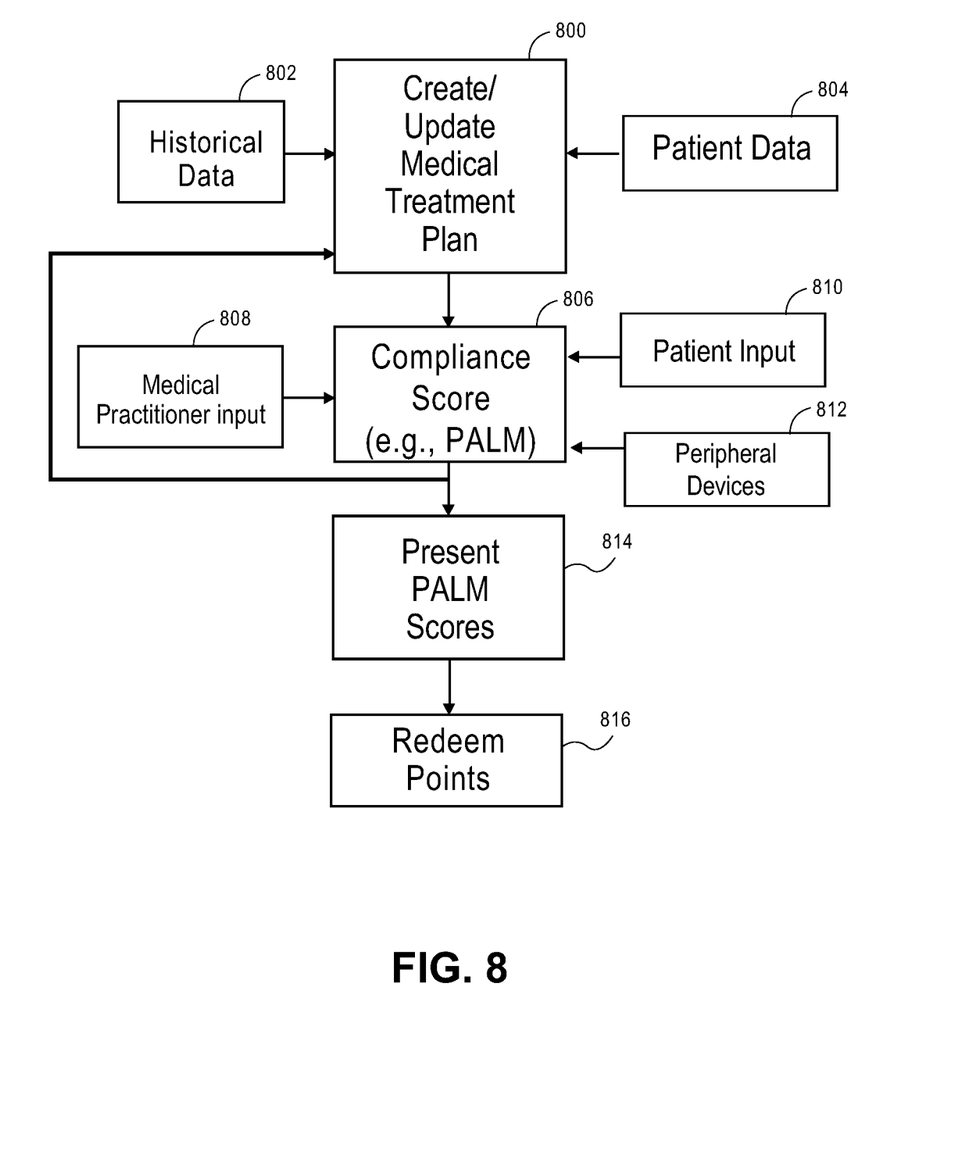
FIG. 8 depicts an exemplary flow diagram of certain methods.

FIG. 8 depicts a flow chart of an exemplary embodiment of the invention. It should be noted that the flow chart is exemplary and not all embodiments of the invention presented above may be incorporated herein. Any blocks of the flow chart may change, be omitted, and other blocks may be added. In block 800 the medical treatment plan is created. The medical treatment plan may be created by the medical practitioner and may incorporate data collected from historical datasets 802 and patient data 804. The medical treatment plan may also be created by a statistical or machine learning algorithm. The medical treatment plan is presented to the medical practitioner and the patient via PALM 806 on a graphical user interface on a computer or mobile device. PALM, in general and as described in the embodiments above, presents multiple factors, or indicators, for measuring the adherence of the patient to the medical treatment plan. Upon evaluating the level of adherence of the patient, a score for each of the multiple indicators, and an overall PALM score, may be calculated. Points may be given based on the individual indicators scores and the overall PALM score. The PALM may be edited by the medical practitioner 808, the patient 810, and may also be updated using peripheral devices 812 as described above. The PALM output is then presented to the patient and the medical practitioner via the GUI at 814. The patient may then redeem the points for any of the rewards described above at 816. The PALM output is also fed back into the medical treatment plan to update the medical treatment plan with the patient's progress and adherence to the plan.

Embodiments of the invention can be configured to operate in a manner that is compliant with regulatory requirements such as HIPPA. A reminder can be used from a third-party application such as or can be integrated into the current invention. The reminders can be tailored for the specific medical treatment plan and individual. Educational content can be provided, including the pearls information, that is conditioned to the individual or otherwise specific to the individual. The invention can also incorporate data from other available datasets, such as consumer behavior, public records, pharmacies, grocery stores, transportation groups and geo-location information, to enhance rewards and customize the look and feel of the user interface, and to stratify individuals and groups for risk. The invention may also calculate in conjunction to the PALM score, the risk of known knowns, known unknowns, and unknown unknowns as an additional indicator of health outcomes for individuals and groups.

The datasets presented above may also provide valuable information for predicting patient behavior. For example, the availability of a public transportation system may influence the patient's ability or willingness to pick up a prescription. Alternative delivery services may be used. These services may also be included in the dataset. A local grocery store stock may be used to help determine the PALM nutrition indicator. Both the strengths and weakness associated with the social behavior and environment may be learned and possibly, through cooperation, managed to improve patient adherence. Purchasing patterns may be used from grocery stores, department stores, convenient stores, restaurants, online stores, or any other behavior tracking that may be useful to predicting and dynamically changing the medical treatment plan and PALM.

In embodiments, when the overall PALM score or one or more of the components to the overall PALM score drops to a predetermined level, a telemedicine session can be instigated to provide live communication between a health care provider and the individual. The telemedicine session can be triggered by a score level, the health care provider, periodically, as an appointment or other event that would be beneficial for the health care provider and the individual to communicate in real time. The telemedicine session can include the interaction between the health care provider and the individual by increasing frequency and removing the requirements that the two need to be physically close in proximity. This results in more frequent feedback between the two and assists in increasing compliance and adherence.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. One or more computer-storage media storing computer-executable instructions that, when executed by a computer system having a processor, perform a method of improving the compliance of at least one patient with a medical treatment plan, the method comprising the steps of:
    receiving, by the processor, the medical treatment plan for the at least one patient, wherein the medical treatment plan is created by a medical practitioner, a statistical algorithm, or a machine learning algorithm;
    receiving and storing, within a data store, a patient profile of the at least one patient;
    presenting the medical treatment plan to the at least one patient via a graphical user interface;
    providing educational information to the at least one patient related to the medical treatment plan via the graphical user interface;
    providing at least one education question to the at least one patient based on the educational information via the graphical user interface;
    determining, by the processor, a first score in response to the an answer provided by the at least one patient to the at least one education question;
    determining, by the processor, a second score based on the at least one patient's attendance of at least one scheduled appointment with a medical practitioner;
    determining, by the processor, a third score in response to at least one lab result of the at least one patient;
    determining, by the processor, a fourth score in response to the at least one patient's documentation of at least one medication taken;
    determining, by the processor, a compliance score for the at least one patient based on the first, second, third, and fourth scores,
    wherein the compliance score comprises a weighting factor for each of the first, second, third and fourth scores, said weighting factor being determined by a medical condition of the at least one patient or a treatment location of the at least one patient;
    wherein the compliance score is indicative of overall adherence of the at least one patient to the medical treatment plan;
    calculating, by the processor, points based at least in part on the first, second, third, and fourth scores and the compliance score;
    displaying the points to the at least one patient via the graphical user interface; and
    facilitating redemption of the points by the at least one patient for at least one of: coupons, groceries, reduced insurance premiums, reduced insurance copays, games, music, and rebates.

2. The media of claim 1, further comprising the step of:
    automatically receiving, by the processor, patient health related data for the at least one patient from a peripheral device.

3. The media of claim 2, wherein the peripheral device is a medical health monitoring device chosen from the group consisting of: a heart monitor, a glucometer, an insulin pump, a thermometer, an infusion pump, an interactive patient bed, a ventilator, and an electronic scale.

4. The media of claim 1,
    wherein the first, second, third, and fourth scores and the compliance score is accessible by an insurance provider,
    wherein an insurance discount is provided to the at least one patient via the graphical user interface based on at least one of the first, second, third, or fourth scores or the compliance score.

5. The media of claim 1, further comprising the step of:
    determining, by the processor, a fifth score based on the at least one patient's diet,
    wherein the fifth score is included in the compliance score calculation.

6. The media of claim 1, further comprising the step of:
    displaying the first, second, third, and fourth scores on the graphical user interface,
    generating alerts based on at least one of the first, second, third, and fourth scores being below a predetermined threshold value,
    wherein the predetermined threshold value is determined by at least one of a medical practitioner, a statistical algorithm, or a machine learning algorithm.

7. The media of claim 1, further comprising the step of obtaining information from available online datasets for the at least one patient.

8. A method of improving the compliance of at least one patient with a medical treatment plan, the method comprising the steps of:
    generating the medical treatment plan;
    presenting the medical treatment plan to the at least one patient via a graphical user interface;
    collecting a plurality of indicators of medical treatment plan compliance by the at least one patient;
    automatically receiving patient health related data for the at least one patient from a peripheral device, wherein the peripheral device is an exercise device or health-monitoring equipment;
    determining, by a processor, a compliance score for the at least one patient based on the plurality of indicators and the received health related data, said compliance score comprising a weighting factor for each of the plurality of indicators, said weighting factor being determined by a medical condition of the at least one patient or a treatment location of the at least one patient,
    wherein the compliance score is indicative of overall adherence of the at least one patient to the medical treatment plan;
    facilitating a reward to the patient based on the compliance score; and
    updating the medical treatment plan based on the plurality of indicators and the compliance score.

9. The method of claim 8, wherein the plurality of indicators comprises: correctly answered questions by the patient, appointments attended by the at least one patient, a medical history of the at least one patient, a laboratory history of the at least one patient, a nutrition history of the at least one patient, and the patient health related data gathered by the peripheral device.

10. The method of claim 8, wherein the medical treatment plan is configured by at least one of a medical practitioner, a statistical algorithm, or a machine learning algorithm.

11. A method of improving the compliance of at least one patient with a medical treatment plan, the method comprising the steps of:
    generating the medical treatment plan;

presenting the medical treatment plan to the at least one patient via a graphical user interface;

collecting a plurality of indicators of medical treatment plan compliance by the at least one patient;

determining a compliance score for the at least one patient based on the plurality of indicators, said compliance score comprising a weighting factor for each of the plurality of indicators, said weighting factor being determined by a medical condition of the at least one patient or a treatment location of the at least one patient, wherein the compliance score is indicative of overall adherence of the at least one patient to the medical treatment plan;

calculating points based on the plurality of indicators and the compliance score by a processor;

displaying the points to the at least one patient via the graphical user interface;

facilitating redemption of the points by the at least one patient for reduced insurance premiums or reduced insurance copays; and updating the medical treatment plan based on the plurality of indicators and the compliance score, wherein the plurality of indicators comprises correctly answered questions by the at least one patient, appointments attended by the at least one patient, a medical history of the at least one patient, and a laboratory history of the at least one patient.

12. The method of claim 11, wherein the medical treatment plan is based at least in part on the patient's medical history and demographics.

13. The method of claim 11, wherein the medical treatment plan is based on an analysis of accumulated historical data from at least one other patient.

14. The media of claim 1, wherein the first, second, third, and fourth scores and the compliance score are viewable by a plurality of other patients, further comprising:
providing a reward to the patient with a highest score in any of the first score, the second score, the third score, the fourth score, or the compliance score.

15. The media of claim 1, wherein the first, second, third, and fourth scores and the compliance score are accessible to at least one medical practitioner.

16. The media of claim 15, further comprising:
providing a graphical user interface to the at least one medical practitioner, whereby the at least one medical practitioner can view the first, second, third, and fourth scores and the compliance score of a plurality of patients at the same time.

17. The method of claim 8, wherein the compliance score is viewable by a plurality of other patients, further comprising:
providing a reward to the patient with a highest compliance score.

18. The method of claim 8, further comprising:
providing a graphical user interface to at least one medical practitioner, whereby the at least one medical practitioner can view the compliance score of a plurality of patients at the same time.

19. The method of claim 11, further comprising:
automatically receiving patient health related data for the at least one patient from a peripheral health-related device.

20. The method of claim 11, wherein the plurality of indicators further comprises:
a nutrition history of the at least one patient or patient health-related data automatically received by a peripheral device.

* * * * *